(12) United States Patent
Seznec (10) Patent No.: US 8,459,129 B2
(45) Date of Patent: Jun. 11, 2013

(54) DEVICE FOR DILUTING OF A SAMPLE (76) Inventor: Stéphane Seznec, Chavagne (FR)

(*) Notice: Subject to any disclaimer, the term of this patent is extended or adjusted under 35 U.S.C. 154(b) by 413 days.

(21) Appl. No.: 12/995,027

(22) PCT Filed: May 26, 2009

(86) PCT No.: PCT/EP2009/056380
§ 371 (c)(1), (2), (4) Date: Nov. 29, 2010

(87) PCT Pub. No.: WO2009/144226
PCT Pub. Date: Dec. 3, 2009

(65) Prior Publication Data
US 2011/0100103 A1  May 5, 2011

(30) Foreign Application Priority Data
May 30, 2008 (FR) ...................... 08 53562

(51) Int. Cl.
*G01N 1/00* (2006.01)
(52) U.S. Cl.
USPC .......................................... 73/863
(58) Field of Classification Search
USPC .......................................... 73/863
See application file for complete search history.

(56) References Cited

U.S. PATENT DOCUMENTS

| 2,853,210 A | 9/1958 | Stewart et al. |
| 3,982,667 A | 9/1976 | Chen |
| 3,994,687 A * | 11/1976 | Engelbrecht ............. 222/63 |
| 4,223,558 A * | 9/1980 | Schmider et al. ......... 74/421 R |
| 4,245,509 A | 1/1981 | Mody et al. |
| 4,300,393 A | 11/1981 | Stearns |
| 4,345,628 A | 8/1982 | Campbell et al. |
| 4,350,186 A | 9/1982 | Schalkowsky et al. |

(Continued)

FOREIGN PATENT DOCUMENTS

| EP | 0 251 754 | 3/1992 |
| EP | 1 029 808 | 8/2000 |

(Continued)

OTHER PUBLICATIONS

English Translation of the International Preliminary Report on Patentability, incorporating the English Translation of the Written Opinion of the ISA, Jan. 18, 2011.

*Primary Examiner* — Hezron E Williams
*Assistant Examiner* — Rodney T Frank
(74) *Attorney, Agent, or Firm* — Harness, Dickey & Pierce, P.L.C.

(57) ABSTRACT

The disclosure relates to a device for diluting a sample, comprising an end-piece for dispensing a liquid diluent, means, having an upright extending upwards from the base, for supporting and moving the end-piece relative to the container support between a first position in which the outlet of the end-piece lies above the opening of the container, to allow the diluent to be fed into the container, and a second position in which the outlet is further away from the container. According to the disclosure, the second position of the outlet is to the side of the first, the upright is fixed to the base, and the upright has a cover at the upper end thereof for supporting the end-piece, the cover being rotatable on the upright between the positions, a rotary drive motor for rotating the cover between the positions being housed on the inside of the cover and/or of the upright.

10 Claims, 5 Drawing Sheets

U.S. PATENT DOCUMENTS

| | | | |
|---|---|---|---|
| 4,844,297 A | 7/1989 | Smith | |
| 6,302,302 B1 | 10/2001 | Albisetti | |
| 6,739,478 B2 * | 5/2004 | Bach et al. | 222/1 |
| 7,000,267 B2 * | 2/2006 | Chesters | 4/620 |
| 2003/0000965 A1 * | 1/2003 | Bach et al. | 222/135 |
| 2005/0006410 A1 * | 1/2005 | Bach et al. | 222/309 |

FOREIGN PATENT DOCUMENTS

| | | |
|---|---|---|
| EP | 1 707 939 | 10/2006 |
| FR | 2 579 749 | 10/1986 |
| GB | 1204474 | 9/1970 |
| GB | 1437552 | 5/1976 |
| GB | 1495662 | 12/1977 |
| WO | WO82/02696 | 8/1982 |
| WO | WO83/02761 | 8/1983 |
| WO | WO 2007/113561 | 10/2007 |
| WO | WO 2008/003689 | 1/2008 |
| WO | WO 2008/003696 | 1/2008 |

* cited by examiner

DEVICE FOR DILUTING OF A SAMPLE

CROSS-REFERENCE TO RELATED APPLICATIONS

This application is a National Phase Entry of International Application No. PCT/EP2009/056380, filed on May 26, 2009, which claims priority to French Application 08 53562, filed on May 30, 2008, both of which incorporated by reference herein.

BACKGROUND AND SUMMARY

The invention relates to a device for dilution of a sample.

Such devices are used to introduce a diluent liquid to a container containing a sample to obtain a prescribed rate of dilution. The resulting mixture, with the sample optionally crushed previously in another device known as a mixer if the sample is solid, must then undergo microbiological analysis by a laboratory. The device normally comprises a support for receiving a container containing the sample, in which an end piece must dispense the diluent liquid.

Different dilution devices are known. Document EP-A-1 707 939 describes a gravimetric dilution device, in which a pocket of diluent is fixed vertically above the opening of the bag containing the sample. A valve is provided on the lower outlet tube of the pocket for dropping diluent into the bag under the control of a control circuit.

U.S. Pat. No. 4,350,186 describes a device for dilution of a sample in a container, for sending diluent liquid to the container via a first rapid valve and a second slow valve supplied with diluent by a tank via a pump. The valves are supported above the container by a metal bar and a horizontal member, the container being arranged on a base comprising a weighing system. The device also comprises a controller having a locking line which is coupled to an interrupter, which is fixed to the chassis of the base and which enables the valves fixed to the horizontal member to operate when the bar is rotated such that the interrupter is closed and the valves are above the container.

Also, devices other than devices for dilution of a sample are also known. Document EP-B-1 029 808 concerns a distribution head for a liquid product, for example a cosmetic substance, in which it is the user who must manually turn positioning means to be able to press on a push-button which is to control opening of a distribution valve of the product. Document WO-2007/113 561 describes a device for preparation of samples using a syringe fixed on a support and actuated by a motor mounted on the support.

U.S. Pat. No. 2,853,210 concerns a device for distribution of liquid from a bottle with an external body which a user must turn manually relative to an internal body to pass between a distribution position and a closed position. Document FR-A-2 579 749 describes an automatic device for sampling and dilution of a liquid product circulating continuously in circuits. Document EP-B-0 251 744 concerns a device for distribution of a fluid, comprising two pumps fixed on the cover of a container, one of which comprises a motor for incrementally metering a specific volume of fluid to be supplied.

An aim of the invention is, in a device for dilution of a sample, to make for easy handling both of the container containing the sample and of the device for introducing the diluent thereto. Another aim is, in a device for dilution of a sample, to prevent the end piece for distribution of the diluent to be contaminated by the sample liquid or by particles of the sample when the dilution operation in the container is completed and when the container has to be withdrawn, due to the fact that the diluent liquid reaches a certain level in the container. Another aim is to improve the ergonomy of the device for dilution of a sample. Another aim is to reduce production costs of the device for dilution of a sample.

The aim of the invention is a device for dilution of a sample, comprising:

at least one support provided on a base for receiving a container having to contain the sample and comprising an upper opening, at least one end piece for distribution of a liquid diluent, comprising an outlet for the diluent, a system for conveying of the diluent in the end piece according to a determined quantity, fitted with control means, means, comprising an upright extending up from the base, for supporting and shifting the end piece relative to the container support between one and the other of a first position, in which the outlet of the end piece is above the opening of the container to enable the diluent to be sent to the container via the end piece, and of a second position, in which the outlet of the end piece is further away from the container than in the first position, characterised in that the second position of the outlet of the end piece is lateral relative to its first position, the upright is fixed on the base relative to the container support, the upright is topped by a cover serving as support of the end piece, the cover being mounted rotatively on the upright between one and the other of the first and second positions, a rotary motor for rotating the cover between one and the other of the first and second positions being housed inside the cover and/or of the upright.

According to embodiments of the invention:

The motor is located in the upper part of the upright under the cover.

The cover comprises an external surface located opposite the external surface of the upper part of the upright.

The end piece has its outlet bent relative to its part serving to attach it to the cover.

The cover comprises at least one member for detachable attachment of the end piece, this attachment member also acting as rotation connection of the cover to the motor.

The motor is capable of turning an axle made solid in rotation with the cover by coupling means for turning the cover and the end piece between one and the other of the first and second positions.

The coupling means comprise a piece fixed on the axle, the cover comprising means for detachable attachment of the end piece, serving also as attachment to the piece fixed to the axle.

The cover comprises first and second stops cooperating with at least one stop member fixed relative to the upright for stopping the rotation of the cover respectively in the first and second positions by support of the stop member respectively against the first and second stops.

The device comprises means for detecting approach of the first position and/or of the second position cooperating with automatic control means for stopping rotation of the motor before the stop member touches the associated stop.

The means for detecting approach are optical for detecting the presence of a hole or wall located in the cover, such that detection of an edge delimiting the hole and the wall corresponds to an angular position of the cover located close to the first and/or second position without the stop member touching the associated stop.

BRIEF DESCRIPTION OF THE DRAWINGS

The invention will be better understood from the following description, given solely by way of non-limiting example in reference to the attached diagrams, in which.

DETAILED DESCRIPTION

In the figures, the dilution device 1 according to the invention comprises a base 2 supporting the different elements of the device, specifically:

a control panel 3 comprising a control monitor 4 and control buttons 5, a support 6 for a container having to contain the sample to be diluted, a weighing system of the contents of the container when it is on the support 6, mechanical connection means 7 being provided between the support 6 and the weighing system, not illustrated, and located inside the base 2, one or more pumps 8, for example peristaltic pumps 81, 82, for example located on one or more sides 21, 22 of the base 2, for sending diluent liquid from a diluent tank, not illustrated, to an associated end piece 91, 92 via pipes 101, 102, flexible in the case of peristaltic pumps, a device 11 for support and displacement of the end piece or end pieces 91, 92.

Of course, any other type of control interface of the operation of the device other than the elements 3, 4 and 5 could be provided.

A single end piece, pipe and associated pump for sending diluent liquid from a single tank to the end piece via the pipe or several end pieces, pipes, pumps and tanks of associated liquid diluents for distributing types of different diluent via the end pieces from the tanks via the pipes can be provided. Hereinbelow, the end piece or the end pieces are designated in general by the reference numeral 9, the associated pipe or pipes by the reference numeral 100, the associated pump or the pumps by the reference numeral 8. The control interface 3, the support 6 and the device 11 are for example located behind one another from front to back on the base 2.

The container having to contain the sample and receive the diluent liquid, not illustrated in the figures, and having to be fixed at least temporarily on the support 6 for introduction of the diluent thereto comprises an upper opening for passage of the diluent and is for example formed by a bag which may be made of supple plastic material. In this case, the support 6 is for example formed by two vertical parallel plates 61, 62, extending for example from the right to the left, spaced apart to create an upper passage and side passages for the container, the two plates 61, 62 being joined together by a lower part 63, for example made in a single piece with the plates, with the lower part being connected to the weighing system.

The weighing system of the contents of the container and the control interface 3 by the user are connected to a conveyor system for conveying of the diluent in the end piece 9 according to a determined quantity, to respect a rate of dilution selected on the interface 3, for example due to the button 5, this rate of dilution being displayed on the monitor 4. The device 11 for support and displacement of the end piece 9 comprises an upright 12 fixed on the base 2, this upright 12 being for example cylindrical and especially circular, as illustrated. The upright 12 is topped by a rotary cover 13 for support of the end piece 9.

Figure 1:
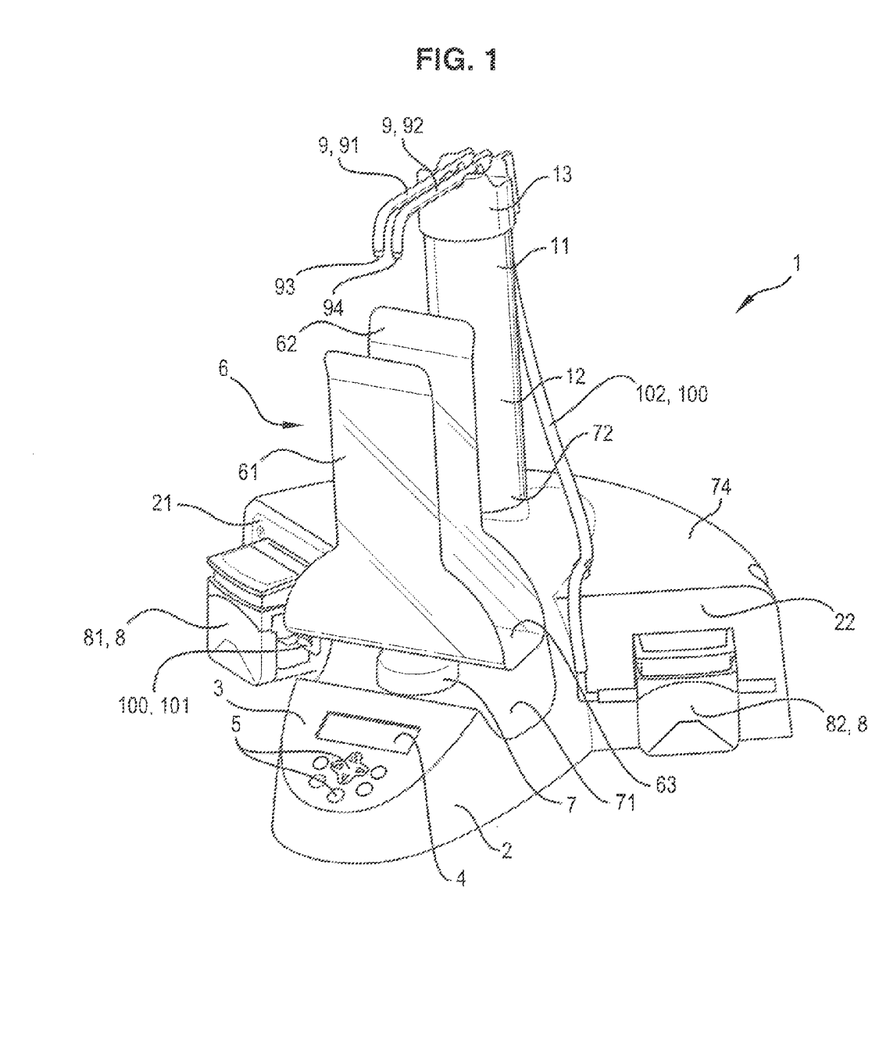
FIG. 1 is a schematic perspective view of an embodiment of the dilution device according to the invention, in a first diluent distribution position.
Figure 2:
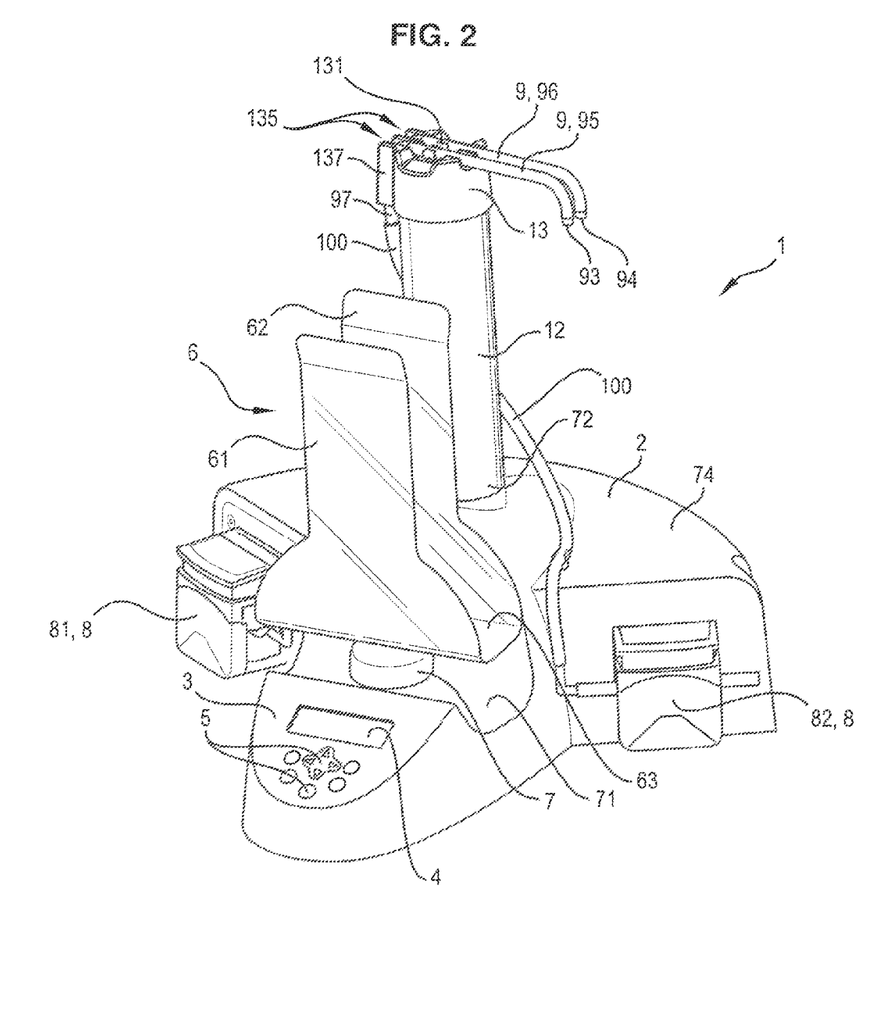
FIG. 2 is a schematic perspective view of the device according to FIG. 1 in a second position of absence of diluent distribution.
Figure 3:
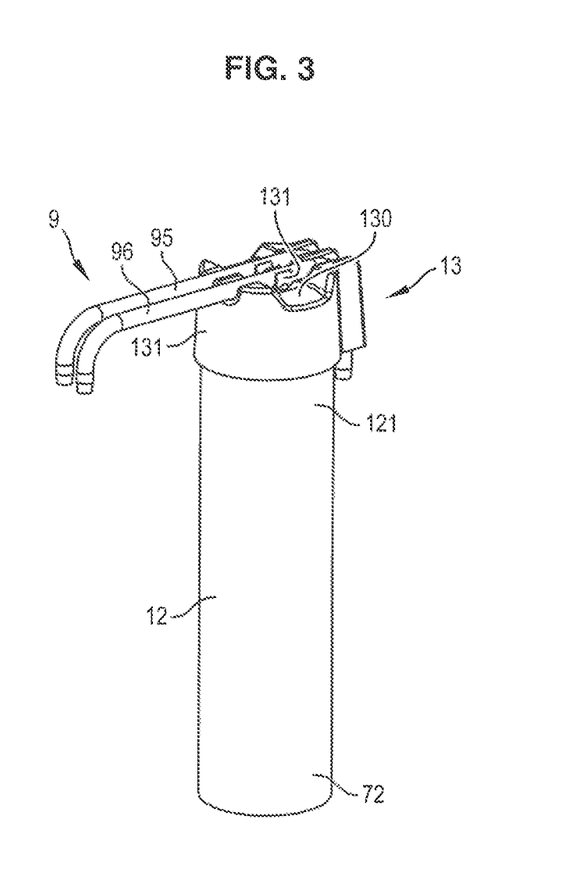
FIG. 3 is a schematic perspective view of the support and displacement device of the end piece for distribution of diluent on the device of FIGS. 1 and 2.
Figure 4:
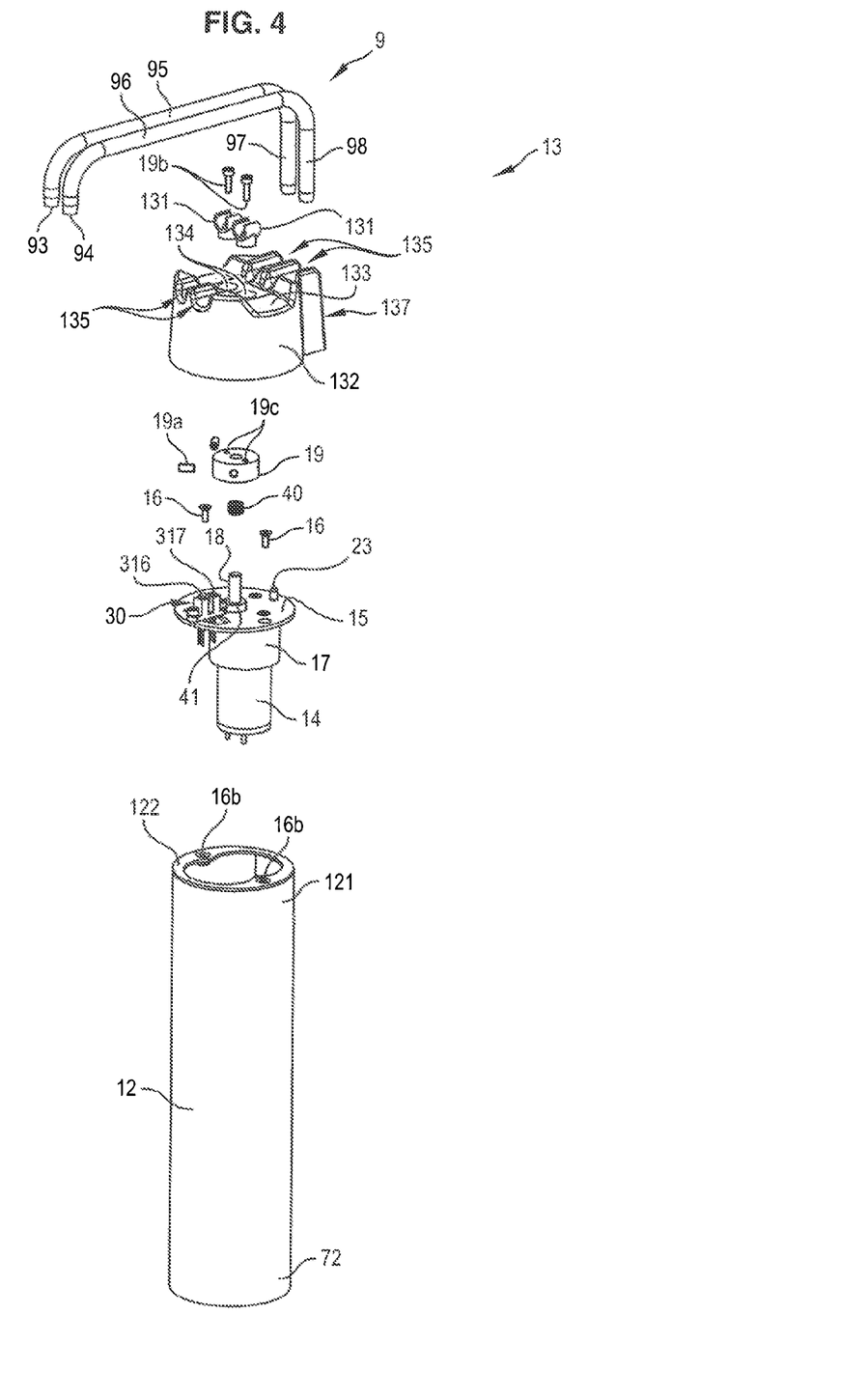
FIG. 4 is a schematic exploded perspective view of the support and displacement device of the end piece according to FIG. 3.

In the second rest position illustrated in FIG. 2, the cover 13 and the end piece 9 are positioned such that the end piece 9 and its diluent outlet 93, 94 are apart from the support 6 of the container, for example in a lateral position to the right (as illustrated) or to the left relative to the support 6 located in front of the upright 12. This second position corresponds to the absence of sending diluent to the end piece 9 and to the stop position of the device. When the user wants to start up the device, he commands the interface 3 to select the rate of dilution he wants and/or to start the device at the rate of dilution imposed thereby. The cover 13 then turns on the upright 12 from the second rest position of FIG. 2 to the first active position illustrated in FIG. 1. In this first position, the outlet 93, 94 of the end piece 9 is above the opening of the container and above the support 6, for example between the plates 61, 62 in the embodiment illustrated.

Actuation means provided in the base 2 automatically operate the pump 8 for sending diluent via the pipe 100 to the end piece 9. The diluent then exits from the end piece 9 via its associated outlet 93, 94 to arrive in the container. The quantity of diluent delivered via the end piece 9 to the container has been automatically calculated by the actuation means as a function of the weighing carried out and the rate of dilution selected by the user, as is known. For example, initial weighing is carried out when the container is empty, a second weighing is completed to determine the weight of the sample having been introduced to the bag, and weighing is carried out during introduction of diluent to the container to respect the quantity of diluent determined as a function of the rate of dilution.

The outlet 93, 94 of the end piece is at a distance from the cover 13 and exceeds the latter. The outlet 93, 94 of the end piece 9 is for example bent relative to its longitudinal part 95, 96 to which it is attached for sending diluent. This longitudinal part 95, 96 is for example that fixed to the cover 13. The cover 13 comprises for example for this purpose on its upper surface 130 means 131 for fixing the end piece 9, for example formed by one or more clips 131 for each end piece 9.

A drive motor 14 for rotating the cover 13 is housed in the upper part 121 of the upright 12. At least the part of the upright 12 located opposite the cover 13 is cylindrical and circular, to allow rotation of the cover 13 relative to this part, formed in the embodiment illustrated by the upper end 122 of the upright 12. In the illustrated embodiment, the cover 13 surrounds the upper part 121 of the upright 12 and is for example formed by a semi-shell, the external wall 132 of which is positioned against the external surface of the upper part 121, preventing liquid accidentally being projected from top to bottom from penetrating the upright 12.

In the illustrated embodiment, the support 6 is supported by the means 7 in a hollow 71 of the top of the base 2 between the upright 12 and the interface 3, for example oriented to the front, preventing liquid accidentally projected to the side of the container from soiling the interface 3 or the rest of the base 2 and the upright 12. The base 72 of the upright 12 is located for example above the edge of the hollow 71, with for example the upper surface 74 of the base 2 between the upright and the hollow 71, inclined to the front, that is, from the upright 12 towards the hollow 71.

The upright 12 is for example hollow from bottom to top and is for example tubular. The motor 14 is fixed in the upright 12 by means of a platen 15 itself fixed to the upper part 21 by attachment means 16. The platen 15 is for example in disc form of a diameter corresponding to the external diameter of the upper end 122 to rest on the top of the upright 12, the attachment means 16 being formed for example by one or more screws fixed in corresponding threads 16b of the end 122. The motor 14 is held by any appropriate means under the platen 15 in the upper part 121 of the upright 12. The motor 14 turns an axle 18 solid in rotation of the cover 13 by means of connection means 19. These rotation connection means 19 are for example formed by a single piece or coupling washer 19 between the axle 18 and the cover 13. In the illustrated embodiment, the washer 19 is fixed, for example by a lateral screw 19a around the axle 18. The clip or the clips 131 or any other attachment means 131 of the end piece 9 to the cover 13 at the same time serve to attach the end piece or end pieces 9 and to attach the end piece or end pieces 9 to the coupling piece 19 and to the rotary axle 18, for example by means of attachment means 19b to the piece 19, such as for example screws 19b passing through the clip or the clips 131 and screwed into threads 19c located on the upper surface of the piece 19, the cover 13 comprising on its upper surface 133 one or more holes 134 for passage and support of clips 131 on their edges. The upper surface 133 of the cover 13 comprises on the one and/or the other of its edges grooves 135 for receiving and positioning the longitudinal part 95, 96 of the associated end piece 9, the means 131 being for example located in the central part of the upper surface 133 between two parts of the grooves 135. At its end away from its outlet 93, 94, the central part 95, 96 of the end piece 9 is prolonged by a bent section 97, 98 attached to the pipe 100 for entry of diluent to the end piece 9. The groove 135 of the rear edge of the cover 13 is prolonged downwards by a groove 137 for receiving and positioning of the entry sections 97, 98 of the end piece 9.

Figure 5:
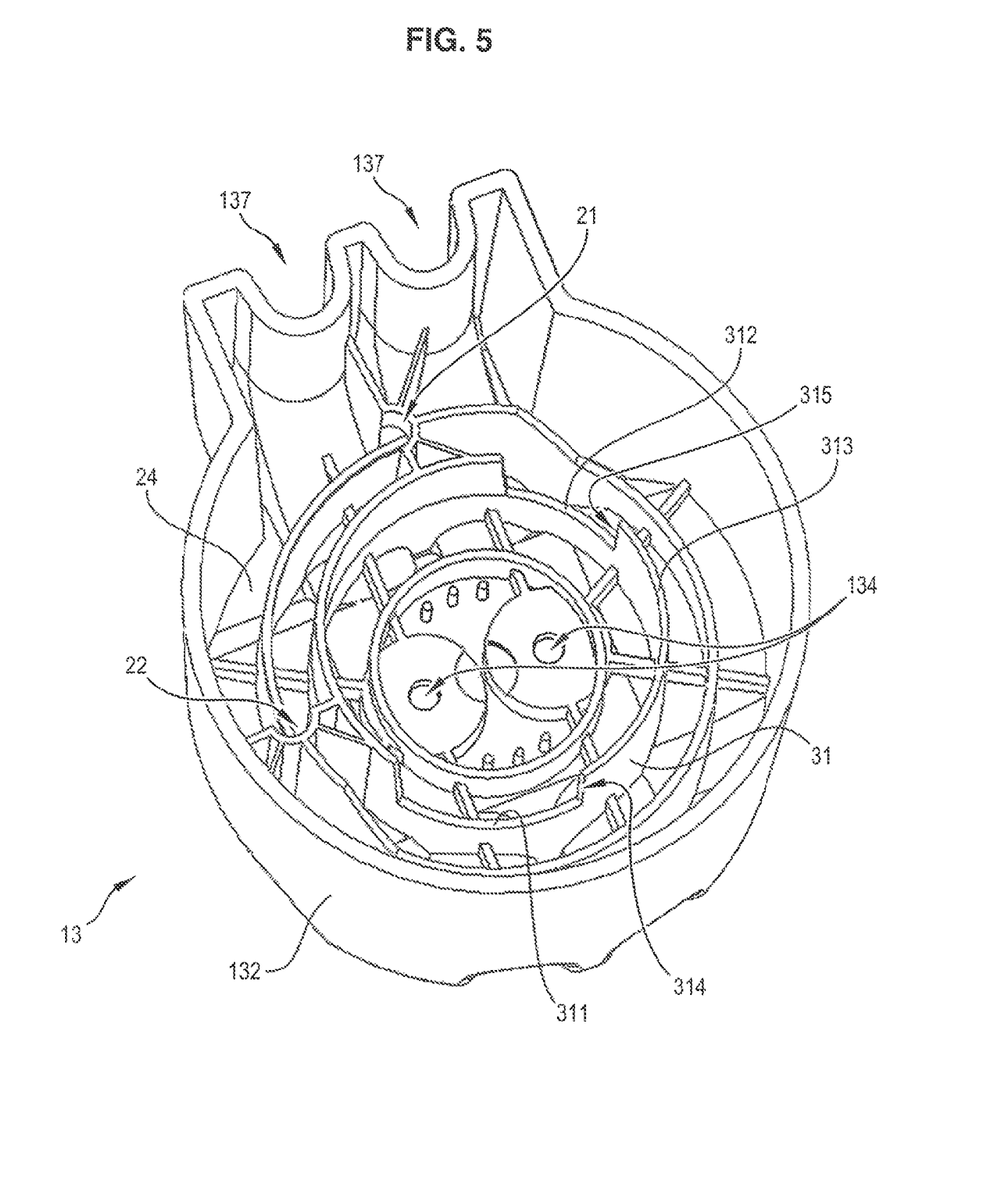
FIG. 5 is a schematic perspective view of the interior of the upper part of the support device of the end piece according to FIGS. 3 and 4.

In the embodiment illustrated in FIG. 5, the inner part of the cover 13 comprises first and second rotation stops 21, 22 respectively in the first and second positions, these stops 21, 22 cooperating with a stop member 23 fixed to the upright 12, formed for example by a pin 23 projecting over the top of the platen 15. A zone 24 for passage of the member 23 between the stops 21 and 22 is provided in the cover 13 during rotation between one and the other of the first and second positions.

Means 30 of detection of approach of the first and second positions of the cover 13 are provided on the upright 12. These approach detection means 30 cooperate for example with corresponding parts 31 located inside the cover 13, whereof they detect displacement in rotation to near the first and second positions. These detection means 30 are for example optical for detecting the presence of walls or holes 31 provided in the cover 13 and positioned relative to the first and second positions. In the illustrated embodiment, a first hole 311 associated with the first position is provided for example, this first hole 311 being separated from a second hole 312 associated with the second position by a wall 313 forming a barrier to the optical signal of the detection means 30, while the holes 311, 312 form no barrier to this detection. The holes 311, 312 and the wall 313 are provided in an inner wall of the cover 13 at least partially surrounding the axle 18. The first edge 314 separating the first hole 311 from the blocking wall 313 is positioned relative to the first stop 21, so as to be met by the means 30 during rotation of the cover 13 from the second position to the first position, before this first position is reached and before the member 23 touches the first stop 21. Similarly, the second edge 315 separating the second hole 312 from the blocking wall 313 is positioned relative to the second stop 22 so as to be met by the means 30 during rotation of the cover 13 from the first position to the second position, before this second position is reached and before the member 23 touches the second stop 22. The means 30 are for example formed by an optical fork fixed to the platen 15 and capable of intercepting the holes 311, 312 and the blocking wall 313 when the latter are between the two teeth 316, 317 of the fork 30 between the first and second positions. Detection by the means 30 of the crossing of the first edge 314 during rotation from the second to the first position triggers, by appropriate automatic means, stopping rotation of the motor 14, causing stoppage of rotation of the cover 13 and of the end piece 9. Detection by the means 30 of the crossing of the second edge 315 during rotation from the first to the second position triggers, by appropriate automatic means, stopping rotation of the motor 14, causing stopping of rotation of the cover 13 and of the end piece 9.

In the illustrated embodiment, elastic means 40 are inserted onto the rotation axle 18 driven by the motor 14 and under the means 19 for coupling to the cover 13, to allow a degree of liberty between them in case of buttressing of the cover 13 on the upright 12, in the event where the motor 14 would not be fully stopped from turning when the member 23 comes against the stop 21 or 22 in arriving in the first or the second position. These means 40 are for example formed by a compression spring, for example helicoidal, threaded about the axle 18 between a lower ring 41 enclosing the base of the axle 18 and the lower surface of the means 19.

Means of electrical connection to the control unit of the device located in the base 12 are provided for electric feed and control of the motor 14 as well as for electric feed and reception of the rotation detection signal sent by the means 30. The motor 14 optionally includes a motor reducer 17 between its rotor and the rotary axle 18 solid in rotation of the cover 13. In response to actuation of the interface 3 by the user, automatic means are provided in the base 12 for shifting the cover 13 and the end piece 9 from the second rest position to the first active position for dispensing diluent, then stopping this dispensing at the prescribed dose, and again moving the cover 13 and the end piece 9 from the first active position to the second rest position.

The invention claimed is:

1. A device for dilution of a sample, comprising:
   at least one support provided on a base for receiving a container having to contain the sample and comprising an upper opening;
   at least one end piece for distribution of a liquid diluent, comprising an outlet for the diluent;
   a system for conveying of the diluent to the end piece according to a determined quantity, fitted with a controller;
   an upright extending up from the base for supporting and shifting the end piece relative to the container support between one and the other of a first position, in which the outlet of the end piece is above the opening of the container to allow sending the diluent to the container via the end piece, and of a second position, in which the outlet of the end piece is further away from the container than in the first position; and
   a rotary motor housed inside at least one of a cover and the upright, for turning relative to the upright the cover serving as support of the end piece for distribution of the diluent liquid between one and the other of the first and second positions, the second position of the outlet of the end piece being lateral relative to its first position, the upright being fixed on the base relative to the container support and being topped by the cover mounted rotatively on the upright between one and the other of the first and second positions.

2. A device as claimed in claim 1, wherein the motor is located in the upper part of the upright under the cover.

3. A device as claimed in claim 1, wherein the cover comprises an external surface located opposite the external surface of the upper part of the upright.

4. A device as claimed in claim 1, wherein the end piece has its outlet bent relative to its part serving as attachment to the cover.

5. A device as claimed in claim 1, wherein the cover comprises at least one member for detachable attachment of the end piece, this attachment member also serving as connection in rotation of the cover to the motor.

6. A device as claimed in claim 1, wherein the motor is capable of turning an axle made solid in rotation with the cover by a coupling for turning the cover and the end piece between one and the other of the first and second positions.

7. A device as claimed in claim 6, wherein the coupling comprises a piece fixed on the axle, the cover comprising a detachable attachment of the end piece, also serving as attachment to the piece fixed to the axle.

8. A device as claimed in claim 1, wherein the cover comprises first and second stops cooperating with at least one stop member fixed relative to the upright for stopping the rotation of the cover respectively in the first and second positions by support of the stop member respectively against the first and second stops.

9. A device as claimed in claim 8, further comprising a detector detecting an approach of at least one of the first position and the second position, cooperating with the automatic controller for stopping the rotation of the motor before the stop member touches the associated stop.

10. A device as claimed in claim 9, wherein the detector is optical for detecting the presence of one of a hole and wall located in the cover, such that detection of an edge delimiting the hole and the wall corresponds to an angular position of the cover located close to at least one of the first and second position without the stop member touching the associated stop.

\* \* \* \* \*